(12) United States Patent
Gill et al.

(10) Patent No.: US 7,460,900 B1
(45) Date of Patent: Dec. 2, 2008

(54) METHOD AND APPARATUS FOR DETECTING ISCHEMIA USING CHANGES IN QRS MORPHOLOGY

(75) Inventors: Jong Gill, Valencia, CA (US); Peter Boileau, Valencia, CA (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 647 days.

(21) Appl. No.: 11/227,856

(22) Filed: Sep. 14, 2005

(51) Int. Cl.
*A61B 5/04* (2006.01)
(52) U.S. Cl. .................................... 600/509; 600/517
(58) Field of Classification Search .................. 607/17, 607/14; 600/509
See application file for complete search history.

(56) References Cited

U.S. PATENT DOCUMENTS

| | | | |
|---|---|---|---|
| 4,712,555 A | 12/1987 | Thornander et al. | 128/419 PG |
| 4,940,052 A | 7/1990 | Mann et al. | 128/419 PG |
| 4,944,298 A | 7/1990 | Sholder | 128/419 PG |
| 5,466,254 A | 11/1995 | Helland | 607/123 |
| 5,476,483 A | 12/1995 | Bornzin et al. | 607/17 |
| 6,016,443 A | 1/2000 | Ekwall et al. | 600/519 |
| 6,377,852 B1 | 4/2002 | Bornzin et al. | 607/9 |
| 6,424,860 B1 | 7/2002 | Karlsson et al. | 600/512 |
| 6,501,983 B1 | 12/2002 | Natarajan et al. | 600/517 |
| 2003/0013974 A1 | 1/2003 | Natarajan et al. | 600/481 |
| 2003/0060854 A1 | 3/2003 | Zhu | 607/25 |

FOREIGN PATENT DOCUMENTS

| | | |
|---|---|---|
| EP | 0 867 146 B1 | 2/2004 |
| WO | WO 00/07497 | 2/2000 |
| WO | WO 03/026740 A1 | 4/2003 |

OTHER PUBLICATIONS

Nearing, Bruce D. et al, "Tracking Cardiac Electrical Instability by Computing Interlead Heterogeneity of T-wave Morphology," J. Appl. Physiol. 95:2265-2272, 2003.

*Primary Examiner*—Carl H. Layno
*Assistant Examiner*—Jon-Eric C Morales

(57) ABSTRACT

A method for operating an implantable medical device includes determining the difference of the absolute value of the voltage of a test QRS complex and the voltage of a baseline QRS template at a plurality of corresponding sample points and detecting ischemia if the sum of the differences at the plurality of sample points is greater than an ischemia detection threshold.

24 Claims, 7 Drawing Sheets

METHOD AND APPARATUS FOR DETECTING ISCHEMIA USING CHANGES IN QRS MORPHOLOGY

FIELD OF THE INVENTION

This invention generally relates to methods and devices for monitoring cardiac electrical activity and more particularly relates to devices and associated methods for detecting, continuously monitoring and treating myocardial ischemia and infarction.

BACKGROUND

Heart failure has become a problem of epidemic proportions in the United States. For example, it is estimated that more than 10 million people in the United States have some form of coronary heart disease. These patients are at risk of myocardial ischemia, i.e. lack of blood supply to different regions of the heart muscle, and/or infarction, i.e. the death of the heart muscle because of ischemic causes. Myocardial ischemia usually manifests itself with angina (i.e. discomfort in the chest) and this, together with evidence coming from laboratory and other investigational methods, leads to the detection of the ischemia.

However, in a large percentage of these patients, episodes of ischemia are asymptomatic (Silent Myocardial Ischemia) and close to one third of infarctions are silent as well. In addition, silent ischemia might progress to myocardial infarction and myocardial infarction is the most common cause of heart failure and/or cardiac death among heart disease patients.

Current techniques for the detection of ischemia are only moderately sensitive and even less specific, especially in certain subgroups of patients. For example, exercise treadmill electro-cardiogram (ECG) testing is one screening technique, but it is only moderately sensitive and has an unacceptably high false positive rate, particularly in the young and in women. In addition, continuous ambulatory ECG monitoring requires a visit to the physician's clinic or hospitalization and can be difficult to interpret because of the large number of artifacts.

Various implantable devices, i.e. cardiac pacemakers or cardiovertors, have been developed to analyze intracardiac electrograms to diagnose the presence and the evolution of an ischemic state in real time, so as to be able to adapt consequently the operation of the device. An intracardiac electrogram signal collected (i.e. sensed or detected) by electrodes coupled to one or more leads implanted in a patient's heart can be used to monitor a series of wave complexes known as the "PQRST" complexes corresponding to the succession of the cardiac beats of the patient. The QRS complex in a cardiac cycle represents the depolarization of the ventricles and is followed by a T wave which represents the repolarization of the ventricle.

The T wave (repolarization wave) amplitude and shape are quite variable, and are sensitive to conduction disturbances in the myocardium and are therefore, often used to detect and monitor the progression of ischemia. For example, elevation of the amplitude of the T-wave (the ST segment) is a significant indicator of cardiac electric instability of the patient. The level of amplitude elevation of the ST segment can therefore be used to detect and monitor the progression of ischemia. However, the ST segment can be affected by conditions other than ischemia, such as food intake, exercise, diabetes and the like reducing the efficacy of ST segment analysis.

SUMMARY

In accordance with one aspect of the present invention a method for detecting ischemia includes determining the absolute value of the difference of the voltage of a test QRS complex and the voltage of a baseline QRS template at a plurality of sample points and detecting ischemia if the sum of the differences at the plurality of sample points is greater than an ischemia detection threshold In another aspect of the present invention an implantable medical device includes a sensing circuit adapted to sense QRS complexes and a microcontroller adapted to determine the absolute value of the difference of the voltage of a test QRS complex and the voltage of a baseline QRS template at a plurality of sample points. In this aspect of the present invention the microcontroller is further adapted to detect ischemia if the sum of the differences at the plurality of points is greater than an ischemia detection threshold.

BRIEF DESCRIPTION OF THE DRAWINGS

Further features and advantages may be more readily understood by reference to the following description taken in conjunction with the accompanying drawings, in which.

DETAILED DESCRIPTION

The invention is described below, with reference to detailed illustrative embodiments. It will be apparent that the invention may be embodied in a wide variety of forms, some of which may be quite different from those of the disclosed embodiments. Consequently, the specific structural and functional details disclosed herein are merely representative and do not limit the scope of the invention.

In one embodiment of the present invention an implantable stimulation device monitors the morphology of the QRS wave to detect ischemia. The present invention may be implemented in connection with any stimulation device that is configured or configurable to monitor intrinsic electrical cardiac activity. However, the advantages of the present invention may be best understood in connection with an exemplary stimulation device that is capable of being used in connection with the various embodiments that are described below.

It is to be appreciated and understood that other stimulation devices, including those that are not necessarily implantable, can be used and that the description below is given, in its specific context, to assist the reader in understanding, with more clarity, the inventive embodiments described herein. In the description that follows, like numerals or reference designators will be used to refer to like parts or elements throughout.

Figure 1:
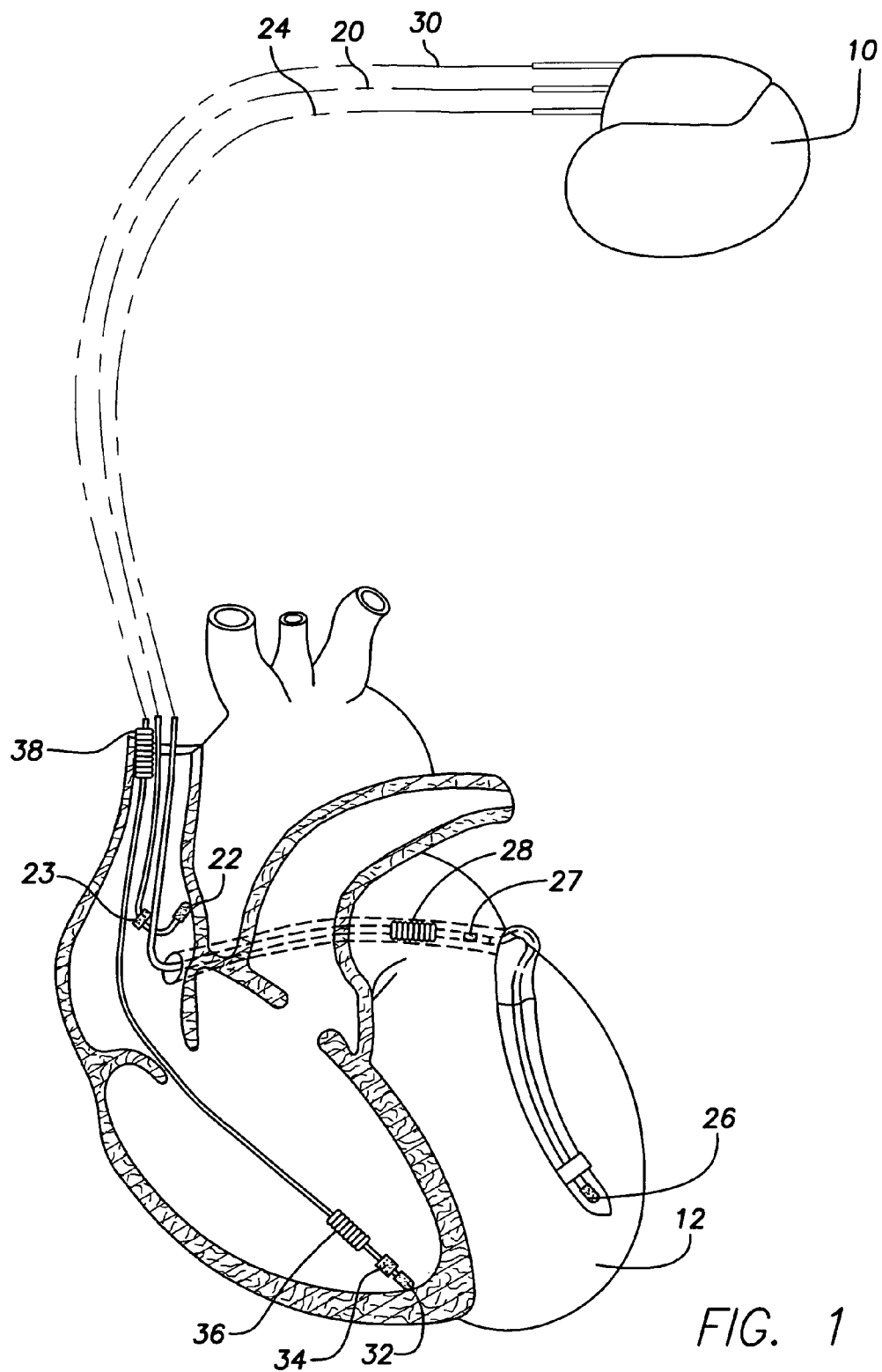
FIG. 1 is a simplified diagram of one embodiment of an implantable stimulation device in electrical communication with a patient's heart for delivering multi-chamber stimulation and shock therapy in accordance with one embodiment of the present invention.

FIG. 1 illustrates a prophylactic defibrillation and stimulation device 10 (also referred to herein as a prophylactic pacer/defibrillator) in electrical communication with a heart 12 by way of three leads 20, 24 and 30, suitable for delivering multi-chamber pacing stimulation therapy and ventricular defibrillation shock therapy. To sense atrial cardiac signals and to provide right atrial chamber stimulation therapy, device 10 is coupled to an implantable right atrial lead 20 having at least an atrial tip electrode 22 and an atrial ring electrode 23, which typically is implanted in the right atrial appendage.

To sense left atrial and ventricular cardiac signals and to provide left chamber pacing therapy, stimulation device 10 is coupled to a coronary sinus lead 24 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28 (or other electrode capable of delivering a shock). For a complete description of a coronary sinus lead, the reader is directed to U.S. Pat. No. 5,466,254, "Coronary Sinus Lead with Atrial Sensing Capability" (Helland), which is incorporated herein by reference.

Stimulation device 10 is also shown in electrical communication with the patient's heart 12 by way of an implantable right ventricular lead 30 having, in this implementation, a right ventricular tip electrode 32, a right ventricular ring electrode 34, a right ventricular (RV) coil electrode 36 (or other electrode capable of delivering a shock), and superior vena cava (SVC) coil electrode 38 (or other electrode capable of delivering a shock). Typically, the right ventricular lead 30 is transvenously inserted into the heart 12 to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of sensing or receiving cardiac signals, and delivering stimulation in the form of pacing and shock therapy to the right ventricle.

Figure 2:
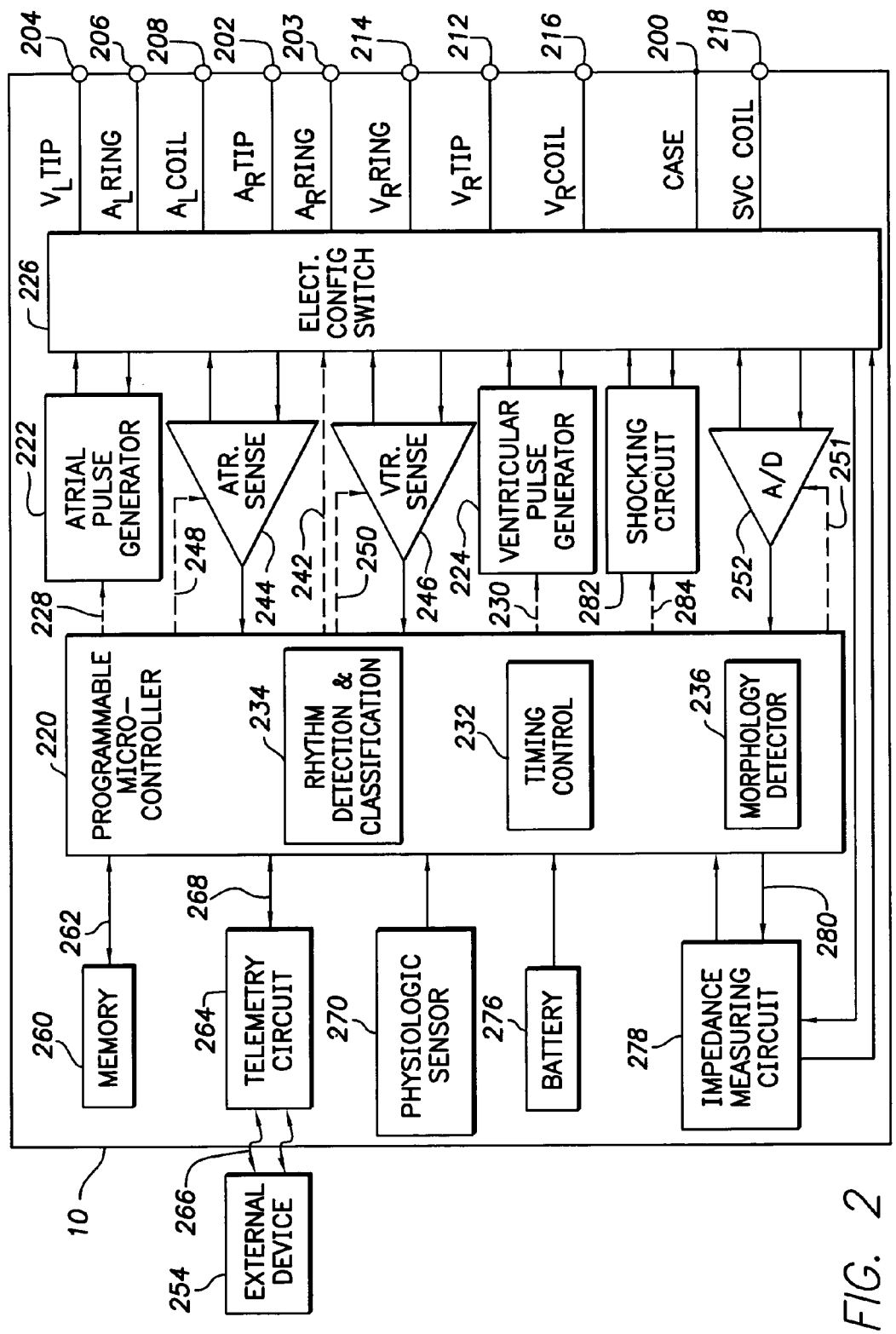
FIG. 2 is a simplified block diagram of a multi-chamber implantable stimulation device configured to provide cardioversion, defibrillation or pacing stimulation or any combination thereof in accordance with one embodiment of the present invention.

FIG. 2 shows an exemplary, simplified block diagram depicting various components of stimulation device 10. The stimulation device 10 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) with cardioversion, defibrillation, and pacing stimulation.

Housing 200 for stimulation device 100 is often referred to as the "can", "case" or "case electrode", and may be selected to act as the return electrode for all "unipolar" modes. Housing 200 may further be used as a return electrode alone or in combination with one or more of the coil electrodes 28, 36 or 38 for shocking purposes. Housing 200 further includes a connector (not shown) having a plurality of terminals 202, 203, 204, 206, 208, 212, 214, 216, and 218 (shown schematically and, for convenience, the names of the electrodes to which they are connected are shown next to the terminals).

To achieve right atrial sensing and pacing, the connector includes at least a right atrial tip terminal (AR TIP) 202 adapted for connection to the atrial tip electrode 22. A right atrial ring terminal (AR RING) 203 may also be included adapted for connection to the atrial ring electrode 23. To achieve left chamber sensing, pacing, and shocking, the connector includes at least a left ventricular tip terminal (VL TIP) 204, a left atrial ring terminal (AL RING) 206, and a left atrial shocking terminal (AL COIL) 208, which are adapted for connection to the left ventricular tip electrode 26, the left atrial ring electrode 27, and the left atrial coil electrode 28, respectively.

To support right chamber sensing, pacing, and shocking, the connector further includes a right ventricular tip terminal (VR TIP) 212, a right ventricular ring terminal (VR RING) 214, a right ventricular shocking terminal (RV COIL) 216, and a superior vena cava shocking terminal (SVC COIL) 218, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry.

Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 20, the coronary sinus lead 24, and/or the right ventricular lead 30 via an electrode configuration switch 226. It is understood that in order to provide stimulation therapy in each of the four chambers of the heart, the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The microcontroller 220 is further coupled to a memory 260 by a suitable data/address bus 262, wherein the programmable operating parameters used by the microcontroller 220 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart 12 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 10 may be non-invasively programmed into the memory 260 through a telemetry circuit 264 in telemetric communication via communication link 266 with an external device 254, such as a programmer, trans-telephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 10 (as contained in the microcontroller 220 or memory 260) to be sent to the external device 254 through an established communication link 266.

The stimulation device 10 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses. While shown as being included within the stimulation device 10, it is to be understood that the physiologic sensor 270 may also be external to the stimulation device 10, yet still be implanted within or carried by the patient.

Examples of physiologic sensors that may be implemented in device 10 include known sensors that, for example, sense respiration rate, pH of blood, ventricular gradient, oxygen saturation, blood pressure and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors to help detect movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 10, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected. Accordingly, the device 10 may employ lithium/silver vanadium oxide batteries.

The stimulation device 10 can further include magnet detection circuitry (not shown), coupled to the microcontroller 220, to detect when a magnet is placed over the stimulation device 10. A magnet may be used by a clinician to perform various test functions of the stimulation device 10 and/or to signal the microcontroller 220 that the external programmer 254 is in place to receive or transmit data to the microcontroller 220 through the telemetry circuits 264.

The stimulation device 10 further includes an impedance measuring circuit 278 that is enabled by the microcontroller 220 via a control signal 280. The known uses for an impedance measuring circuit 278 include, but are not limited to, lead impedance surveillance during the acute and chronic phases for proper performance, lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

Cardiac signals are also applied to inputs of an analog-to-digital (A/D) data acquisition system 252. The data acquisition system 252 is configured (e.g., via signal line 251) to acquire intracardiac electrogram signals, convert the raw analog data into a digital signal, and store the digital signals for later processing and/or telemetric transmission to an external device 254. The data acquisition system 252 is coupled to the right atrial lead 20, the coronary sinus lead 24, and the right ventricular lead 30 through the switch 226 to sample cardiac signals across any pair of desired electrodes.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 20, coronary sinus lead 24, and the right ventricular lead 30, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations.

The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 10 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia.

The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

In the case where the stimulation device 10 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220.

Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 200 may act as an active electrode in combination with the RV coil electrode 36, and/or as part of a split electrical vector using the SVC coil electrode 38 or the left atrial coil electrode 28 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 10 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

The microcontroller 220 is further adapted to analyze the digitized intracardiac electrogram signals output by the data acquisition system to detect the onset or evolution (i.e. progression or regression) of ischemia. In one embodiment the microcontroller compares the digitized intracardiac electrogram signals to a baseline template stored in the implanted device to detect myocardial ischemia.

The onset and or evolution of an ischemic condition alters the depolarization and repolarization characteristics of the heart. For example, an ischemic region in the ventricle of the heart slows down the propagation of the excitation wave through the ventricles and is evidenced by changes in the QRS complex which models excitation wave propagation through the ventricles. Therefore, one embodiment of the present embodiment monitors digitized intracardiac electrograms to detect changes in the morphology of the QRS complex to identify the onset of an ischemic condition. In this embodiment the change in the QRS complex is proportional to the severity of the ischemia.

Figure 3:
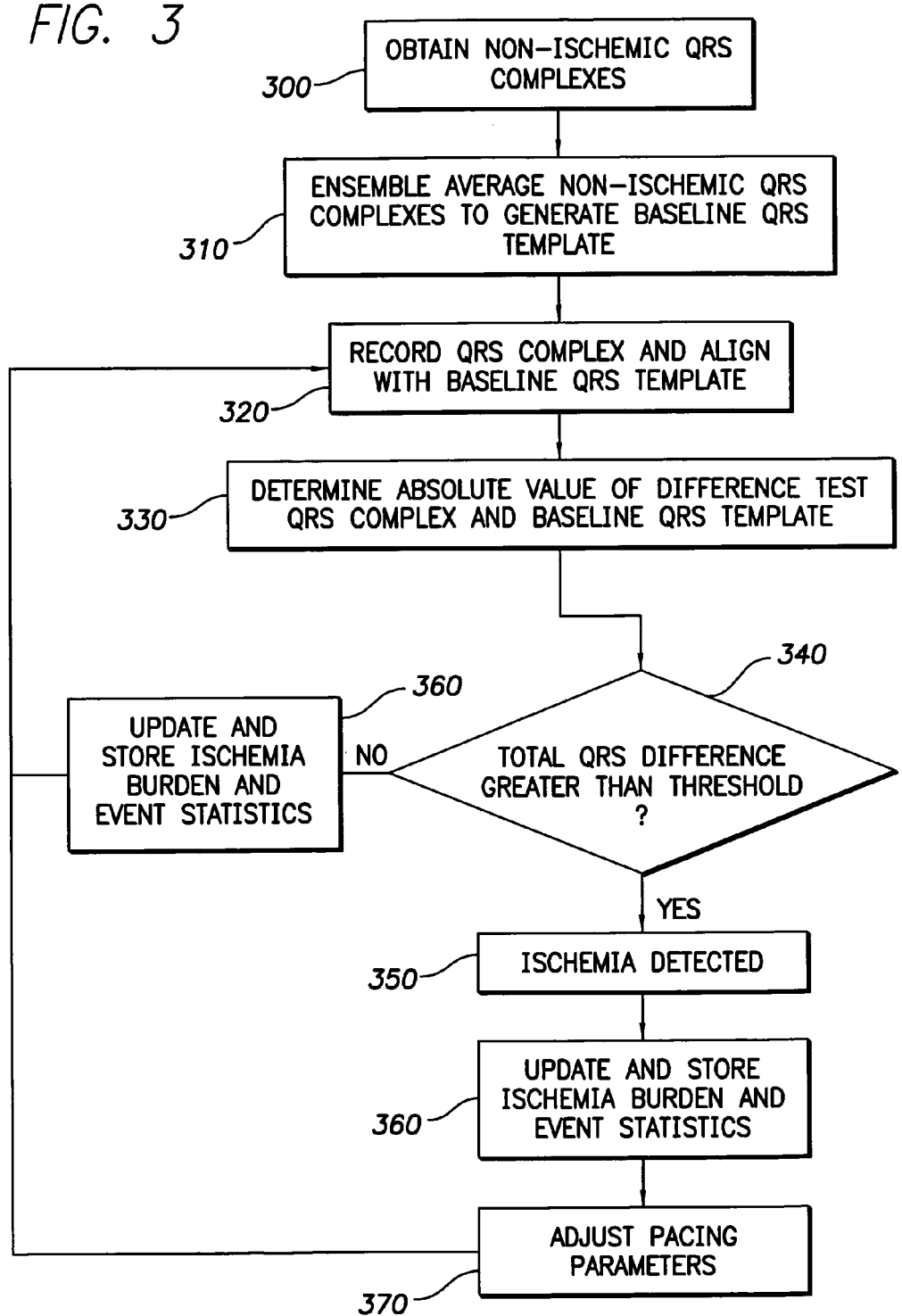
FIG. 3 is a flow chart illustrating a method to detect ischemia in accordance with one embodiment of the present invention.

For example, FIG. 3 is a flowchart illustrating the operation of one embodiment of a stimulation device to detect the onset or progression of ischemia as a function of changes in the amplitude of the voltage of the QRS complex. In this flow chart, the various operational steps are summarized in individual "blocks". Such blocks describe specific actions or decisions that are carried out during operation of the illustrated device 10. Where a microcontroller (or equivalent) is employed, the flow chart presented herein provides the basis for a "control program" that may be used by such a microcontroller (or equivalent) to effectuate the desired control of the stimulation device.

In one embodiment of the present invention the microcontroller, either automatically or under the control of the treating physician, records a plurality of digitized baseline (non-ischemic) QRS complexes 300. Various digital signal processing techniques may be employed for the analysis, such as using first and second derivatives to identify the start and end of the QRS waves.

In one embodiment the complexes are typically recorded for a pre-determined time period beyond the onset of the Q-wave. In this embodiment the microcontroller aligns the maximum amplitude points of the recorded complexes and calculates an ensemble average of the time sampled complexes to generate a baseline QRS template which is stored in memory 310 for subsequent comparison purposes.

The present invention utilizes both paced and intrinsic events to detect an ischemic condition. Therefore, in some embodiments the microcontroller generates separate baseline QRS templates for paced and intrinsic events. In these embodiments, paced and intrinsic measurements are not combined to generate a baseline template but are evaluated separately.

In operation the micro-controller then periodically performs an ischemic test by recording a digitized paced or intrinsic ventricular depolarization (e.g. QRS complex) for comparison to the appropriate paced or intrinsic baseline QRS template. In one embodiment the microcontroller aligns the maximum amplitude of the baseline QRS template with the maximum amplitude of the QRS complex under test 320. Alternatively, the microcontroller may record a plurality of consecutive or nearly consecutive QRS test complexes and ensemble average the recorded plurality of test complexes which is then used in the comparison test.

Figure 4:
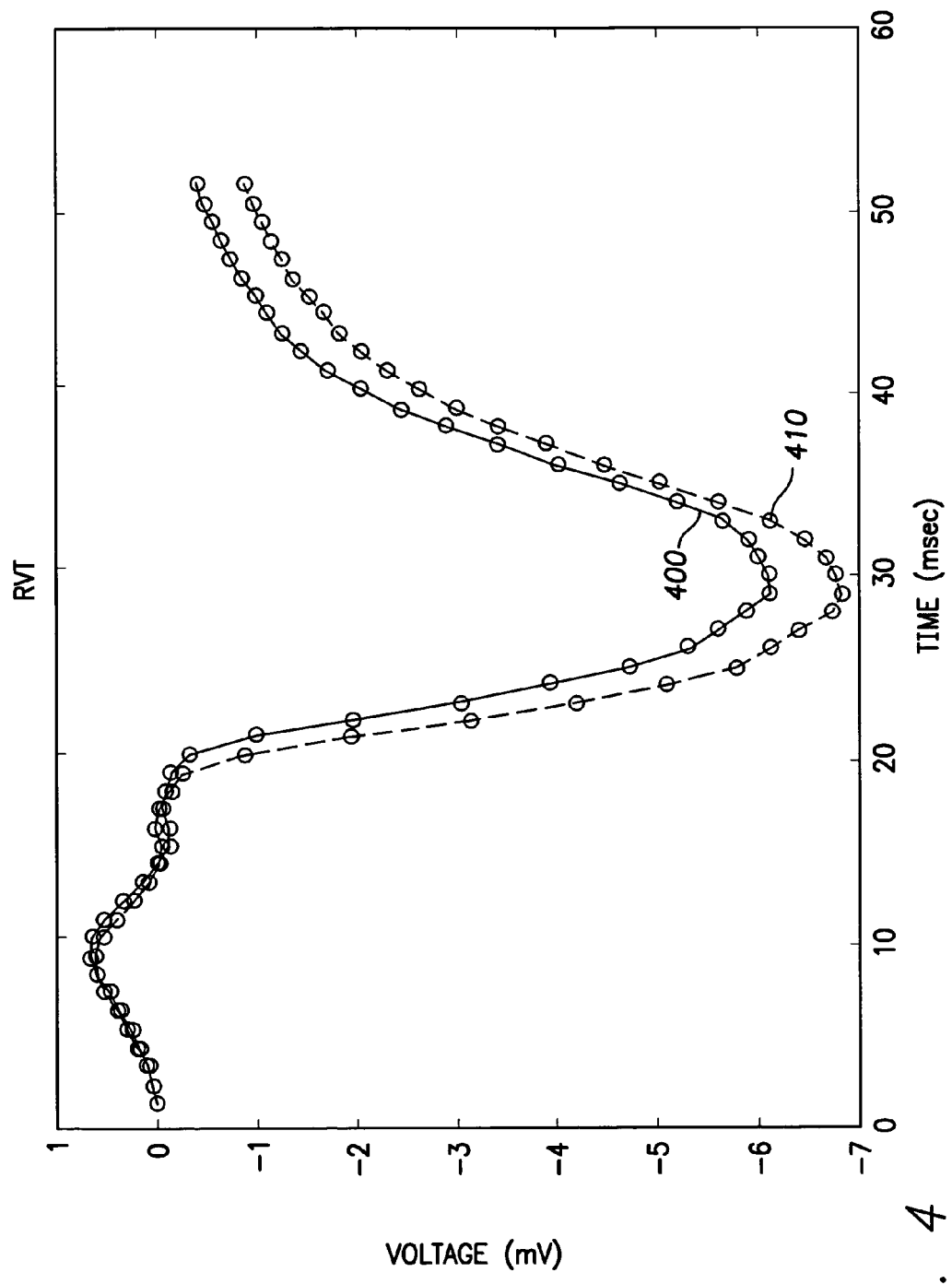
FIG. 4 is a graphical illustration of a baseline QRS complex and an ischemic QRS complex resulting from a forced occlusion.

The microcontroller then determines, by way of example, the absolute value of the difference in voltage amplitude at each of the sample points of the digitized QRS complexes 330. For example, FIG. 4 graphically compares the ensemble average of multiple baseline (non-ischemic) QRS complexes 400 measured on a unipolar right ventricular tip (RVT) electrode in a canine with an ischemic QRS complex 410 measured on the same electrode as a function of time. In this instance the ischemic QRS complex was recorded approximately five minutes into the occlusion of the proximal region of the left arterial descending artery (LAD) of the canine. The effects of the occlusion on the propagation of the excitation wave through the ventricles are seen in the variation between the voltage of the ischemic QRS complex and the voltage of the baseline complex.

Figure 5:
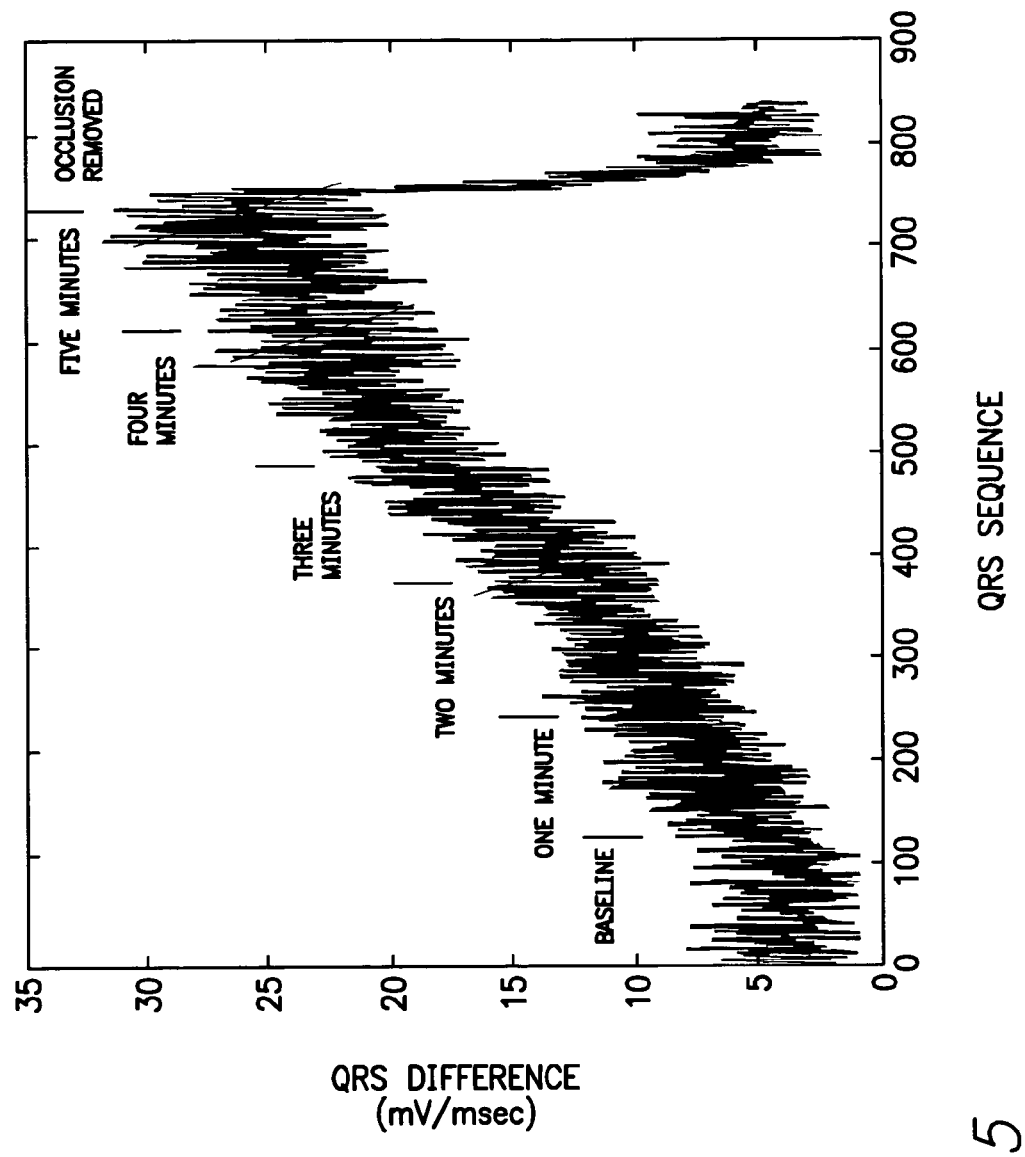
FIG. 5 is a graphical illustration of the total QRS difference between a baseline QRS complex and an ischemic QRS complex as a resulting from a forced occlusion as a function of length of the occlusion.

Further, the magnitude of the change in voltage provides an indication of the severity of the ischemic condition. For example, FIG. 5 graphically illustrates the trend of the total QRS difference values (i.e. the sum of the absolute value of the difference at each of the sample points of a digitized baseline complex and an ischemic complex) for a series of QRS complexes over the course of a five minute forced occlusion of the proximal region of the left arterial descending artery (LAD) of a canine. The measured data was again collected on a unipolar right ventricular tip (RVT) electrode in the canine.

In this example, there is relatively little difference between the baseline QRS (i.e. no occlusion shown for approximately the first 110 sequences) and the stored QRS template. However, the total QRS difference between baseline and ischemic complexes gradually increases as the duration of the occlusion increases, reaching a maximum of approximately 30 mVms at the end of five minutes. In this illustrative example the occlusion was removed after minutes and the QRS difference converges relatively quickly to the non-ischemic values.

Returning to FIG. 3, in one embodiment the microcontroller therefore sums the absolute value of the difference at each sample point of the baseline QRS templates and a single QRS complex and compares the total QRS difference to a programmable threshold 340. If the total QRS difference is greater than the programmable threshold value ischemia is detected 350. In one embodiment of the invention the QRS template is not redefined or updated after ischemia is detected to allow for the documentation of the long term progression of the ischemic burden.

Alternatively, the microcontroller can calculate the total QRS difference for each of several consecutive or approximately consecutive QRS complexes. In this embodiment the microcontroller calculates various statistics, such as, by way of example, the statistical mean, variance and the like, of the total QRS differences and compares the mean or variance of the total QRS difference to a threshold to detect the onset of ischemia.

The ischemia detection threshold is, by way of example, programmable and may vary depending upon the application, patient condition and physician preference. Further the interval at which ischemia diagnoses are performed also depends on the application.

For example, in some embodiments the microcontroller measures the ischemia burden approximately every one to two hours to generate a long-term diagnostic record. In this instance the microcontroller records a QRS complex every hour and compares the digitized QRS complex to a baseline QRS template determined at a single point in time (e.g. at implant or at the command of a clinician). Alternatively, the long term ischemic burden may be monitored by determining the total difference value for the recorded complex and a baseline QRS template in the form of an average of a plurality of baseline QRS templates recorded over a relatively long period of time (e.g. a long term moving average taken over the previous week).

In the context of acute ischemia event detection, the microcontroller in one embodiment determines the total QRS difference on a more regular basis, for example, approximately every 30-60 seconds. In this context, the microcontroller determines the baseline QRS template from a relatively recent history. For example, in some embodiments the microcontroller computes the baseline QRS template from a short term moving average of QRS complexes periodically measured over the previous hour.

In this instance acute myocardial ischemia is indicated if the calculated total QRS difference between the QRS complex under test and the baseline template exceeds a programmable threshold. In some embodiments an ischemic event is detected if only one QRS difference measurement exceeds the threshold. In other embodiments the detection of an ischemic event requires several consecutive complexes (e.g. 3-5) having a total QRS difference value that exceeds the threshold. Alternatively ischemia detection may require that the total QRS difference value for a predetermined percentage (e.g. 3 out of 5) of consecutive QRS complexes exceed the threshold.

Further, in some embodiments the microcontroller utilizes a measure of statistical significance (e.g. T-statistic) between the baseline and subsequent measurements compared to a threshold to verify the detection of an ischemic event using the total QRS difference value. Similarly, in other embodiments the microcontroller monitors the width of the QRS complex and verifies ischemia detection if the width of the complex under study is greater (by a predetermined amount of time) than the baseline QRS template or greater than a threshold value.

A long-term record of the patient's ischemia burden obtained through continuous monitoring is a useful adjunct to current methods of ischemia detection and diagnosis. Such a record may reveal infrequent or unprovokable ischemia perhaps associated with nascent coronary artery disease, vasospasm or embolism as well as trends in the progression or regression of coronary artery disease. A long-term record of ischemia burden can also be used to gauge the efficacy of, and/or patient compliance with, a course medication.

Therefore, in one embodiment, the microcontroller generates an ischemia burden metric for tracking the evolution of the ischemia. The burden metric in one embodiment is the ratio of periodic measurements for which ischemia is indicted relative to the total number of periodic measurements. In this embodiment the microcontroller stores and updates the ischemia burden, and any other clinically significant event statistics such as the total QRS difference, heart rate, activity rate, or the like in device memory upon completion of the ischemia diagnostic test 360.

In some embodiments the ischemia burden metric includes an indication of the certainty of the detection and/or the severity of the ischemia. In one embodiment for example, the degree by which a feature exceeds its threshold for ischemia detection is mapped to a severity/likelihood index. In some embodiments, low value for the severity/likelihood index values indicate the threshold for detection was barely exceeded and high values indicate the threshold was exceeded by at least a predetermined percentage. In these embodiments the burden metric tracks the number of ischemia event detections and the severity level of each detected event.

The event log and/or the recorded electrogram exhibiting the ischemia may be downloaded at a later time to a clinician for analysis via an external programmer. The clinician is then able to use this information in making subsequent treatment decisions.

Ischemia is a condition resulting from insufficient blood flow through the heart muscle. Because myocardial perfusion occurs primarily during the diastolic phase, lower heart rates, which have correspondingly longer diastolic phase, are conducive to increased perfusion while high heart rates have the potential of exacerbating an ischemic condition. Therefore, in some embodiments the microcontroller automatically adjusts the pacing mode or pacing parameters in response to the detection of an ischemic condition to ensure that the heart is not paced at a rate that might worsen the ischemic effects 370.

For instance, in one embodiment the microcontroller automatically switches to a non-tracking pacing mode in response to the detection of an ischemic condition. Alternatively, the microcontroller may adjust various pacing parameters in response to the detection of an ischemic condition. For example, in one embodiment the microcontroller automatically decreases the maximum tracking rate to limit the rate at which the ventricles can be paced regardless of the atrial rate to ensure that the heart is not paced at a rate that exacerbates the ischemic condition.

The microcontroller may also automatically adjust the maximum pacing rate during rate-adaptive pacing in response to the detection of cardiac ischemia. Typically, a rate responsive cardiac stimulation device increases its pacing rate (up to a maximum sensor rate) in response to increases in the patient's activity level. The rate of this change is referred to as the aggressiveness of the rate response.

However, in an ischemic state, the aggressiveness of the rate response may provide for a pacing rate that exacerbates the ischemic effects. Accordingly, in some embodiments of the present invention the microcontroller adaptively reduces the maximum sensor rate or increases the atrio-ventricular (AV) delay in response to the detection of an ischemic state.

In addition, in some embodiment, the implantable device forces the ventricular rate lower than the sinus rate through special pacing techniques such as the one described in commonly owned U.S. Pat. No. 6,377,852, entitled "Implantable Cardiac Stimulation Device And Method For Prolonging Atrial Refractoriness" by Bornzin, Sloman, Boileau and Florio, the content of which is incorporated herein by reference as if set forth in full. Conversely, when an ischemic state is no longer detected, the adapted variables are incrementally returned toward its original value. Accordingly, ischemia can be minimized while still maintaining the rate responsive features of the implantable cardiac stimulation device.

One of skill in the art will appreciate that the sample length and sampling rate used to generate the QRS complexes can affect the performance of the classification system. For example, varying the sampling rate creates tradeoffs between the response time of the detection system and the sensitivity and specificity of the detection system as well the computational duty cycle of the detection algorithm.

Further the QT interval typically varies with heart rate. Therefore in some embodiments, the micro-controller adjusts the pacing therapy to provide appropriate conditions for the diagnosis for ischemia. For example, the microcontroller may invoke AV hysteresis (i.e. lengthening or shortening of the AV delay) to encourage V-pacing or inhibition if primarily paced or intrinsic events are desired for the ischemia diagnosis. In a ventricular resynchronization therapy device, V-V timing may also be adjusted.

Similarly, the microcontroller may slow the pacing rate to a target rate if it is currently elevated, e.g. due to rate response for activity level. Further, the pacing rate may be slightly increased to a target rate temporarily to provoke ischemia in case myocardial oxygen demand is on the verge of exceeding supply.

In some embodiments the microcontroller optionally confirms that favorable conditions for ischemia detection exist and if not, e.g. if the intrinsic rate is too fast, a measurement is not made at this time. Rather the existence of unfavorable conditions is optionally logged.

Figure 6:
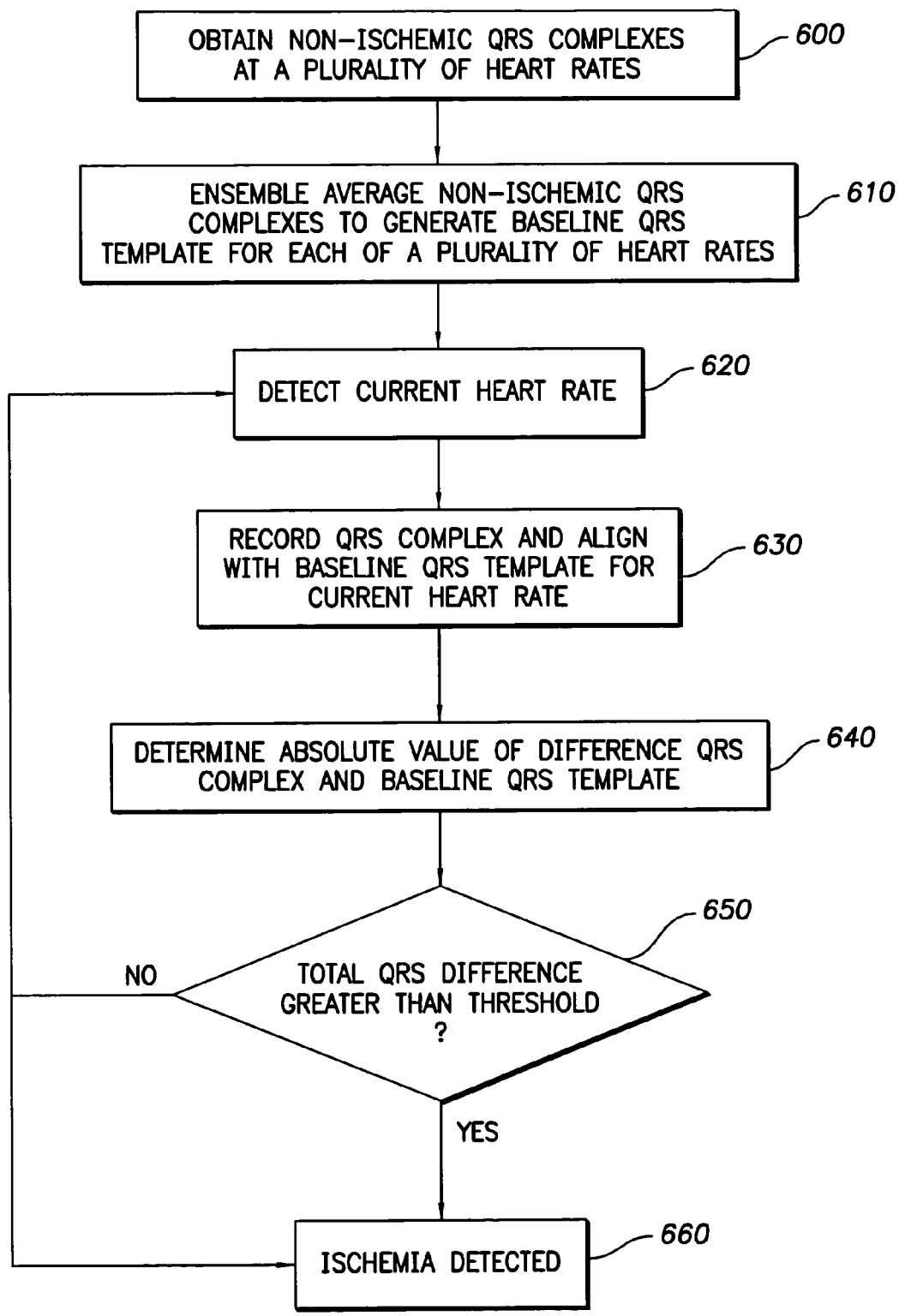
FIG. 6 is a flow chart illustrating a method to detect ischemia over a range of heart rates in accordance with one embodiment of the present invention.

In other embodiments the microcontroller normalizes the QRS difference values as a function of heart rate to provide ischemia diagnostic capability over a range of heart rates. For example, referring to the flow chart in FIG. 6, in one embodiment of the present invention the microcontroller, either automatically or under the control of the treating physician, records a plurality of digitized (non-ischemic) QRS complexes 600 at each of a plurality of heart rates. In this embodiment, digital signal processing techniques, such as, by way of example, first and second derivative calculations, may again be used to identify the start and end of the QRS waves at each of the plurality of heart rates.

In one embodiment the complexes are typically recorded for a pre-determined time period beyond the onset of the Q-wave for each of the plurality of heart rates in accordance with the variation of the QRS width as a function of heart rate. In this embodiment the microcontroller calculates an ensemble average of the time sampled complexes for each of the plurality of heart rates to generate a baseline QRS template for each heart rate which is stored in memory 610 for subsequent comparison purposes.

When performing an ischemic test the device first determines the current heart rate 620 then records a digitized QRS complex for comparison to the stored baseline QRS complex corresponding to the current heart rate. In one embodiment the microcontroller aligns the maximum amplitude of the baseline QRS template with the maximum amplitude of the QRS complex under test 630.

The microcontroller then determines, by way of example, difference of the amplitude of the voltage at each sample point of the QRS complexes 640. The microcontroller then sums the absolute value of the difference at each sample point and compares the total QRS difference to a programmable threshold 650. If the total QRS difference is greater than the programmable threshold value ischemia is detected 660.

In other embodiments the microcontroller utilizes multiple sensing vectors (e.g. RV ring to case, LV ring to case, or the like) to improve sensitivity and/or specificity. In some instances multi-site characterization provides the ability to reveal a pattern unique to ischemia and different from patterns which might be produced by other confounding influences. In addition, multi-site measurements provide a rough indication of the location of the occlusion in the heart.

Figure 7:
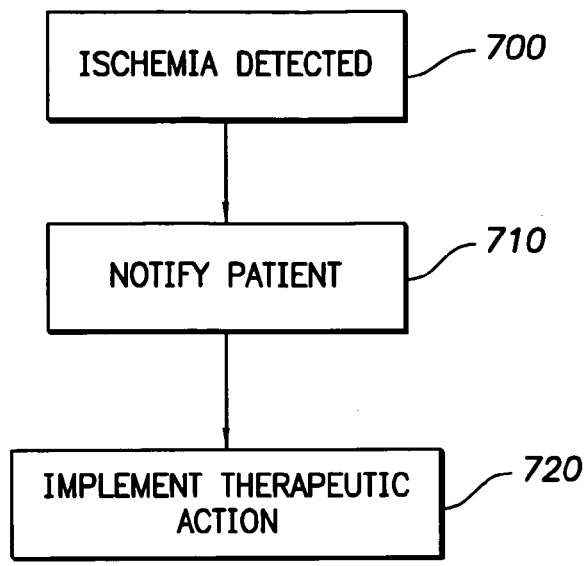
FIG. 7 is a flow chart illustrating a method for responding to the detection of an ischemic event in accordance with one embodiment of the present invention.

Referring to FIG. 7, in some embodiments of the present invention the implantable stimulation device may alert the patient 710 of the detection of an ischemic condition 700 so that the patient can take appropriate action such as taking medication, ceasing exertion, lying down, etc. The implantable device may utilize an audio or vibratory signal to alert the patient. Alternately, the device may telemeter an alert message to an external device which subsequently conveys the message to the patient or to an external monitoring center.

In addition, some embodiments of the present invention include the ability to implement a therapeutic action 720 in response to the detection of an ischemic condition. For example, the microcontroller may initiate the infusion of a thrombolytic agent or anticoagulant agent in response to the detection of an ischemic event to prevent more serious medical complications.

While the invention herein disclosed has been described by means of specific embodiments and applications thereof, numerous modifications and variations could be made thereto by those skilled in the art without departing from the scope of the invention set forth in the claims. For example, the methods or algorithms described in connection with the embodiments disclosed herein may be embodied directly in hardware, in a software module executed by a processor, or in a combination of the two.

A software module may reside in RAM memory, flash memory, ROM memory, EPROM memory, EEPROM memory, registers, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention.

Figure 8:
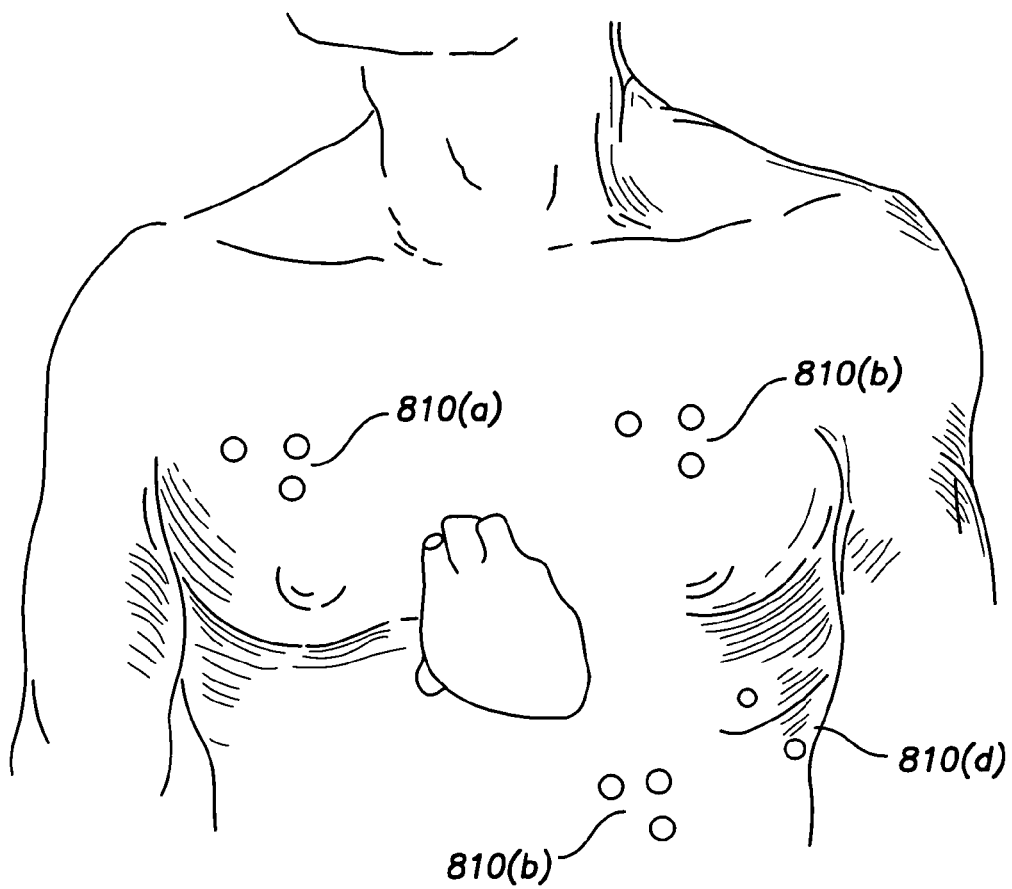
FIG. 8 is a frontal view of a patient in whom an loop recorder may be implanted with typical locations referenced thereon.

For example, in some instances a physician may wish to practice the present invention in a minimally invasive device which does not utilize an implantable intracardiac lead to perform multi-vector sensing of cardiac depolarization signals. For instance, in one embodiment the present invention may be utilized in an external holter monitor or in an implantable loop recorder as depicted in FIG. 8.

An implantable loop recorder, in accordance with one embodiment of the invention, includes two or more electrodes, each of which is capable of sensing cardiac depolarizations. In one embodiment, a standard ECG monitoring system may be used as a screening device to optimize the implant site locations 810(a-d) for the loop recorder. Further, orthogonal measurements over each candidate implant site may also be performed to determine the optimal electrode orientation at each implant site.

The implantable loop recorder may then be inserted into a subcutaneous pocket at the identified location and with the optimized orientation. The implantable loop recorder then continuously records the patient's subcutaneous ECG to generate a digitized QRS complex. The loop recorder compares the digitized QRS complex with a baseline QRS template stored in the loop recorder to detect the onset of ischemia or track the long term ischemic burden as previously described.

In other embodiments the present invention may be practiced with lead-less devices which are capable of performing multi-vector sensing of cardiac depolarization signals. Thus, the present invention is not intended to be limited to the embodiments shown herein but is to be accorded the widest scope consistent with the principles and novel features disclosed herein.

What is claimed is:

1. A method for detecting ischemia, comprising:
generating a baseline QRS template;
determining absolute value of difference of voltage of a test QRS complex and voltage of the baseline QRS template at a plurality of sample points; and
detecting ischemia if a sum of the differences at the plurality of sample points is greater than an ischemia detection threshold.

2. The method of claim 1 wherein generating a baseline QRS template comprises generating an ensemble average of a plurality of digitized baseline QRS complexes.

3. The method of claim 1 further comprising aligning the test QRS complex with the baseline QRS template.

4. The method of claim 1 wherein aligning the test QRS complex with the baseline QRS template comprises aligning maximum amplitude of the test QRS complex with maximum amplitude of the baseline QRS template.

5. The method of claim 1 further comprising generating and storing an ischemia burden metric.

6. The method of claim 1 further comprising adjusting cardiac pacing parameters to increase heart perfusion in response to detection of ischemia.

7. The method of claim 1 wherein generating a baseline QRS template comprises generating a baseline QRS template at each of a plurality of heart rates.

8. The method of claim 7 further comprising determining current heart rate and wherein determining total difference of absolute value of amplitude of a test QRS complex and amplitude of the baseline QRS template at a plurality of sample points comprises determining total difference of absolute value of amplitude of a test QRS complex and amplitude of the baseline QRS template corresponding to the current heart rate.

9. The method of claim 1 further comprising notifying patient of detection of ischemia.

10. The method of claim 1 wherein generating a baseline QRS template comprises generating a baseline QRS template for each of a plurality of sensing vectors and wherein determining total difference of absolute value of amplitude of a test QRS complex and amplitude of the baseline QRS template at a plurality of sample points comprises determining total difference of absolute value of amplitude of a test QRS complex sensed with each of the plurality of sensing vectors with the amplitude of the corresponding baseline QRS template for that sensing vector.

11. The method of claim 10 wherein detecting ischemia if the absolute value of the difference is greater than an ischemia detection threshold comprises detecting ischemia if the absolute value of the difference for each of the plurality of sensing vectors is greater than an ischemia detection threshold.

12. The method of claim 1 wherein generating a baseline QRS template comprises generating a short term moving average of a plurality of digitized baseline QRS complexes.

13. The method of claim 1 wherein generating a baseline QRS template comprises generating a long term moving average of a plurality of digitized baseline QRS complexes.

14. An implantable medical device, comprising:
means for generating a baseline QRS template;
means for determining absolute value of difference of voltage of a test QRS complex and voltage of the baseline QRS template at a plurality of sample points; and
means for detecting ischemia if a sum of the differences at the plurality of sample points is greater than an ischemia detection threshold.

15. The implantable medical device of claim 14 wherein the means for generating a baseline QRS template comprises means for generating an ensemble average of a plurality of digitized baseline QRS complexes.

16. The implantable medical device of claim 14 further comprising means for aligning the test QRS complex with the baseline QRS template.

17. The implantable medical device of claim 14 further comprising means for generating and storing an ischemia burden metric.

18. The implantable medical device of claim 14 further comprising means for adjusting cardiac pacing parameters to increase heart perfusion in response to the detection of ischemia.

19. The implantable medical device of claim 14 further comprising means for determining a current heart rate, wherein the means for generating a baseline QRS template comprises means for generating a baseline QRS template at each of a plurality of heart rates and wherein the means for determining total difference of absolute value of amplitude of a test QRS complex and amplitude of the baseline QRS template at a plurality of sample points comprises means for determining total difference of absolute value of amplitude of a test QRS complex and amplitude of the baseline QRS template corresponding to the current heart rate.

20. The implantable medical device of claim 14 wherein the means for generating a baseline QRS template comprises means for generating a baseline QRS template for each of a plurality of sensing vectors and wherein the means for determining total difference of absolute value of amplitude of a test QRS complex and amplitude of the baseline QRS template at a plurality of sample points comprises means for determining total difference of absolute value of amplitude of a test QRS complex sensed with each of the plurality of sensing vectors with the amplitude of the corresponding baseline QRS template for that sensing vector.

21. The implantable medical device of claim 20 wherein the means for detecting ischemia further comprises means for locating zone of ischemia as a function of each of the plurality of absolute value of difference values.

22. An implantable medical device, comprising:
a pulse generator adapted to deliver a plurality of pacing pulses to a patient's heart;
a sensing circuit adapted to sense QRS complexes; and
a microcontroller adapted to determine absolute value of difference between voltage of a test QRS complex and voltage of a baseline QRS template at a plurality of sample points and to detect ischemia if a sum of the differences at the plurality of sample points is greater than an ischemia detection threshold.

23. The implantable medical device of claim 22 wherein the microcontroller is adapted to ensemble average a plurality of digitized baseline QRS complexes to generate the baseline QRS template.

24. The implantable medical device of claim 23 wherein the microcontroller is further adapted to adjust cardiac pacing parameters to increase heart perfusion in response to detection of ischemia.

* * * * *